United States Patent [19]

Mierzwa et al.

[11] Patent Number: 5,780,442
[45] Date of Patent: Jul. 14, 1998

[54] ORTHOSOMYCINS FROM MICROMONOSPORA CARBONACAE

[75] Inventors: Ronald A. Mierzwa, Bloomfield; Min Chu, Union; John K. Jenkins, Chatham; Mahesh G. Patel, Verona, all of N.J.

[73] Assignee: Schering Corporation, Kenilworth, N.J.

[21] Appl. No.: 604,692

[22] Filed: Feb. 21, 1996

[51] Int. Cl.$^6$ ............................. A61K 31/71; C07H 15/00
[52] U.S. Cl. .................. 514/25; 314/23; 314/53; 314/54; 536/16.8; 536/18.1; 536/18.7; 536/123; 536/123.1
[58] Field of Search ............... 536/16.8, 18.1, 536/18.7, 123, 123.1; 574/54, 53, 25, 23

[56] References Cited

U.S. PATENT DOCUMENTS

| | | | |
|---|---|---|---|
| 4,597,968 | 7/1986 | Waitz et al. | 424/118 |
| 4,622,314 | 11/1986 | Ganguly et al. | 574/54 |
| 4,767,748 | 8/1988 | Ganguly et al. | 574/54 |

FOREIGN PATENT DOCUMENTS

WO 87/02366   4/1987   WIPO.

OTHER PUBLICATIONS

Tetrahedron Letters, vol. 36, No. 24, 1995 pp. 4163–4166, S. Kalliney, et al..
Heterocycles, vol. 28, No. 1, 1989, pp. 83–88, Ganguly, et al.
Kirk–Othmer, Encyclopedia of Chemical Technology, 4th edtion, 1992, vol. 3, Antibiotics (Oligosaccharides) pp. 259–266.

*Primary Examiner*—Elli Peselev
*Attorney, Agent, or Firm*—Mathew Boxer; John J. Maitner

[57] ABSTRACT

Orthosomycins have been isolated from the fermentation broth of the microorganism *Micromonospora Carbonacea var Africana* designated SCC 2146. These compounds are antibacterial agents. Compositions and methods for treating bacterial infections are also described.

15 Claims, 8 Drawing Sheets

ORTHOSOMYCINS FROM MICROMONOSPORA CARBONACAE

SUMMARY OF THE INVENTION

Compounds A, B, C, D, E, F, G, H and J have been isolated from the fermentation broth of the microorganism *Micromonospora Carbonacea var Africana* designated SCC 2146. These compounds were identified as orthosomycins. These compounds are antibacterial agents. A component from the culture, compound A, was found to be the most potent antibacterial agent.

The invention relates to novel antibacterial compounds A, B, C, D, E, F, G, H and J, and their preparation, and to compositions containing such compounds. This invention also relates to a fermentation broth of the microorganism *Micromonospora Carbonacea var Africana*, and the component parts thereof obtainable by cultivation of a pure culture of *Micromonospora Carbonacea var Africana*.

The invention relates to the microorganism *Micromonospora Carbonacea var Africana*. Another aspect of the invention is directed to the antibiotic complex produced by cultivating a strain of *Micromonospora Carbonacea var Africana* in a pH and temperature controlled aqueous nutrient medium having assimilable sources of carbon and nitrogen under controlled submerged aerobic conditions until a composition of matter having substantial antibiotic activity is produced. A major component of the culture of the present invention is antibiotic 13-384, component 1, as disclosed in U.S. Pat. No. 4,597,968, which is hereby incorporated by reference. (Another major component of the culture is the corresponding nitroso analog.) However, the present invention claims other compounds of the culture as described below.

The present invention is also related to an antibiotic composition comprising a pharmaceutically acceptable carrier and an antibiotically effective amount of one or more compounds selected from the group consisting of compounds A, B, C, D, E, F, G, H and J. The present invention is also related to a method of treating a bacterial infection which comprises administering an antibiotically effective amount of one or more compounds selected from the group consisting of compounds A, B, C, D, E, F, G, H and J.

DETAILED DESCRIPTION OF THE INVENTION

FERMENTATION OF THE MICROORGANISM

Figure 1:
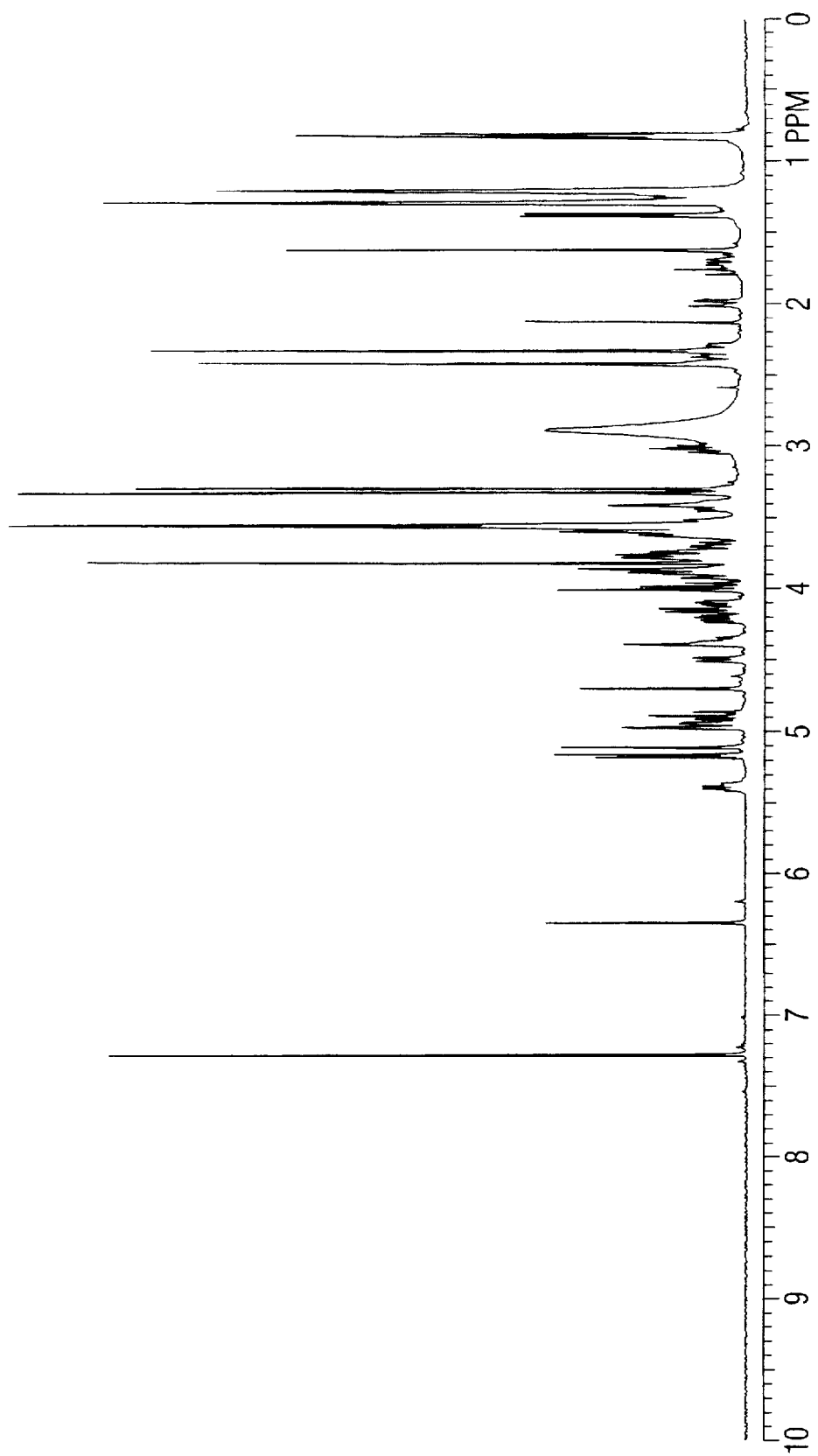
FIGS. 1, 2, 4, 6, 7 and 8 are proton NMR spectra for Compounds A, B, E, F, G, H, and J, respectively.

One mL frozen culture of *Micromonospora carbonacea* subspecies Africana, strain PF6-3 was transferred into a 300 mL Erlenmeyer shake flask containing 100 mL of seed medium. The medium composition (g/L) was as follows: beef extract (Difco) 3, Tryptone (Difco) 5, Cerelose (CPC, 2001) 1, potato dextrin (Avebe, WPD-650) 24, yeast extract (Universal, Tastone) 5, calcium carbonate (Pfizer, Albaglos) 1, and silicone defoamer (Union Carbide, SAG-471, 30% suspension) 0.3 mL/L. The flask was incubated 48 hours at 30° C. with agitation (300 rpm, 1 inch stroke), and 30 mL of the culture were transferred to 6×2 L flasks, each containing 500 mL of the same seed medium. Following 48 hours of incubation as before, the 3 L culture was transferred into an inoculation fermenter containing 300 L of the same medium for an additional 24 hours of cultivation. Finally, the contents of the inoculation fermenter were transferred to a larger fermenter containing 10,000 L of production medium. The composition of the production medium (g/L) was as follows: yeast extract 5, meat peptone (Marcor, type PS) 6, Cerelose 22, corn steep powder (Marcor) 2, potato dextrin 60, boiled linseed oil (Kleenstrip) 4, calcium carbonate 4, cobalt chloride•6 $H_2O$ (Mallinckrodt) 0.002, silicone defoamer 0.5 mL/L. The fermentation was conducted at 36° C. for 120 to 140 hours under aeration and agitation maintaining the dissolved oxygen between 50 to 100% saturation. The fermentation was carried out with 80–240 standard cubic feet per minute air flow for about 120–130 hours.

ISOLATION

The fermentation broth was cooled to about 25° C. One half of the fermentation broth was transferred to a separate vessel, agitated and adjusted with 2N NaOH to pH 10.5. A 300 L XAD-7 resin (Rohm & Haas non functional acrylic ester polymeric adsorbent) was charged to the fermentation broth and agitated for 0.5 hours. The pH was lowered to 9.25 and agitated for 3.5 hours. The pH was further lowered to 7.00, and the resin was separated form the broth by screening. Tap water was used to wash the resin free from both broth and mycelia. The second half of the fermentation broth was processed in the same way.

About 300 L of adsorbed resin was charged to a 500 L tapered column containing 100 L deionized water. The resin was washed with upflow. After dropping the aqueous level to the resin bed, the resin was washed downflow with 900 L of deionized water. The antibiotic was eluted from the resin downflow by charging the column with 900 L ethyl acetate (pre-washed with 140 L of 0.1M sodium phosphate monobasic buffer, adjusted to pH 8 with sodium hydroxide) at 10 L/minutes. The eluate was collected in 150 to 200 L cuts. The antibiotic complex containing cuts were combined and extracted with 140 L of 0.1M sodium phosphate monobasic, adjusted to pH 8 with sodium hydroxide, then with 2×60 L deionized water. The ethyl acetate layer was vacuum concentrated at less than 30° C. to one tenth the original volume (about 50 L) with azeotropic distillation of residual water. The concentrate was precipitated into 100 L of heptane (2 volumes). The precipitate was filtered and dried at about 25° C. in a vacuum oven using a nitrogen bleed to give 5.2 to 5.5 kg of crude material (2.6 to 3.1 kg of antibiotic complex).

OXIDATION

With agitation, 10 to 11 kg of the crude antibiotic complex were dissolved in 10 volumes of 80/20 ethyl acetate-acetone to oxidize the nitroso component of the complex of the antibiotic 13-384. Two kilograms of sodium bicarbonate and 50 g of vanadyl acetyacetonate catalyst were added. 5.5 L tert-butyl hydroperoxide, (3M solution in 2,2,4-trimethyl pentane) were added slowly over 0.5 hour while the temperature was maintained at 25° to 30° C. The progress of the oxidation was monitored by by HPLC (high pressure liquid chromatography). Additional catalyst was added when needed and agitation of the reaction mixture was continued until the reaction was complete.

INITIAL PURIFICATION

Approximately 2.5 kg of crude oxidized material was dissolved in 9 L of ethyl acetate and applied to the head of a 10 foot by 1 foot diameter column packed with 70 kg of bare irregular silica gel (70 to 250 µm) in isopropyl acetate (The solvent can also be 80/20 ethyl acetate/heptane). The column was eluted with isopropyl acetate at a flow rate of 5 to 7 L/minute at 35 pounds per square inch gauge. Fractions 1, 2, and 3 were collected as 200 L cuts. The antibiotic components were monitored by HPLC and TLC. The solvent used for TLC chromatographies was 9:1 methylene chloride-methyl alcohol. Fractions 5 to 11 which were enriched in the main antibiotic component were combined and vacuum concentrated to about 6 L at less than 30° C. The main cut was isolated by adding the concentrate to 2 volumes of heptane with agitation. The precipitate was filtered and dried in a vacuum oven at about 25° C. with a nitrogen bleed to obtain 1.2 kg of product. The head cut fractions 3 and 4 which were enriched in impurities were preocessed in a simlar manner to obtain 0.4 kg of product. The tail cut fractions 12 to 15 which were enriched in impurities, were preocessed in a similar manner to obtain 0.2 kg of product.

Further Purification of the Antibiotic Complex

The purification was accomplished in a two step chromatographic procedure. Both head (ID 33285-104-2) and tail cuts (ID 33285-104-1) obtained from initial purification were first chromatographed under medium pressure conditions with diol-bonded silica gel (40–63µ irregular media). The column was equilibrated with a ternary mixture of $CH_2Cl_2$:Heptane:MeOH (60:40:2 v/v/v) at a flow rate of 30–50 mL/min. with nitrogen gas. After sample application, 2.4 L–2.8 L of mobile phase was collected and discarded. The mobile phase was then adjusted and fractions collected based on diol column bed volume. Fractions containing new components were then purified with semi-preparative high pressure liquid chromatography on PVA-Sil (polyvinyl alcohol functionalized silica gel), with peak collection based on UV signal monitoring at 265 nm. For individual component purifications, minor mobile phase adjustments were made (see Scheme 1).

Example #1

Five grams of enriched tail cut (ID 33285-104-1) were dissolved in 20 mL of $CH_2Cl_2$:MeOH (96:4 v/v) and applied to 200 g (~400 mL) of pre-conditioned diol-bonded silica (40–63µ, irregular media) contained in a glass column (600×50 mm, 1.18 L). The diol column conditioning step prior to sample application involved the passage of 1 L of MeOH followed by 1.2 L of initial mobile phase $CH_2Cl_2$:Heptane:MeOH (60:40:2 v/v/v). After sample application, 2.4 L of mobile phase was collected after which time the ratio of mobile phase was adjusted to 75:25:2 and maintained for an additional 8 L. Individual fractions were obtained and evaluated for the presence of minor components by analytical HPLC under the following isocratic conditions: PVA-Sil, 5µ, 15 cm×4.6 mm $CH_2Cl_2$:MeOH (98:2)/20 minutes. Complex 1 yielded 200 mg of material containing 15% of a new component, Compound A, that is less polar than antibiotic, 13-384, component 1. Complex 1 was further purified by dissolving 30–40 mg of the sample in 0.5 ml $CH_2Cl_2$:MeOH (96:4 v/v) and injecting on a semi-preparative PVA-Sil column (250×20 mm) equilibrated with $CH_2Cl_2$:MeOH (97.5:2.5 v/v). A flow rate of 12 mL/min yielded 5 mg of the desired material within a 12–14.2 minute elution time window. After four additional injections were made, a total of 24 mg of Compound A (>98% pure) was obtained.

Complex 2 (100 mg) was further purified by using the same semi-preparative HPLC conditions described as above except a $CH_2Cl_2$:Heptane:MeOH (78:20:2, v/v/v) solvent system was used as the mobile phase. Two pure components, Compound E (1.5 mg) and Compound F (9.5 mg) were obtained. However, the first component (2.4 mg) was identified as a mixture of two compounds, Compound C and Compound D, based on analysis of spectroscopic data.

Example #2

Five grams of enriched head cut (ID 33285-104-2) was dissolved in 25 mL of $CH_2Cl_2$:MeOH (96:4 v/v) and applied to a recycled 200 g diol-bonded silica gel column. Recycling involved passing 1.5 L of MeOH followed by 1.5 L of starting mobile phase $CH_2Cl_2$:Heptane:MeOH (60:40:2 v/v/v). After sample application, 2.8 L of mobile phase was collected and effluent discarded. Mobile phase was adjusted to 75:25:2 (v/v/v) and 400 mL fractions were collected. Based on analytical HPLC, four fractions were pooled as complex 3, and yielded 360 mg of a yellowish powder after rotary evaporation. (The rest of the fractions were pooled as complex 4.) HPLC analysis of complex 3 on PVA-Sil indicated two peaks with elution times earlier than Compound A. Optimization studies for preparative chromatography led to the selection of a binary solvent system composed of n-butylchloride:MeOH which revealed the presence of a third entity. Approximately, 40–45 mg of complex 3 was then dissolved in 1.0 mL of $CH_2Cl_2$:MeOH (96:4 v/v) and injected on a semi-preparative PVA-Sil column (250×20 mm) equilibrated with n-butylchloride:MeOH (93:7 v/v). Flow rate was 15 mL/minutes and UV detection was at 265 nm. Three components were collected. The first two components (9.5 mg and 11.5 mg) were unstable and could not be identified. Only the third component (39 mg) was identified as Compound B.

Complex 4 (61 mg) was further purified by a modified semi-preparative HPLC method similar to the conditions described above but with a different mobile phase of $CH_2Cl_2$:MeOH (97.5:2.5, v/v). Three pure components, Compound G (6.1 mg), Compound H (8.7 mg) and Compound J (27.5 mg) were obtained from this complex.

SCHEME 1

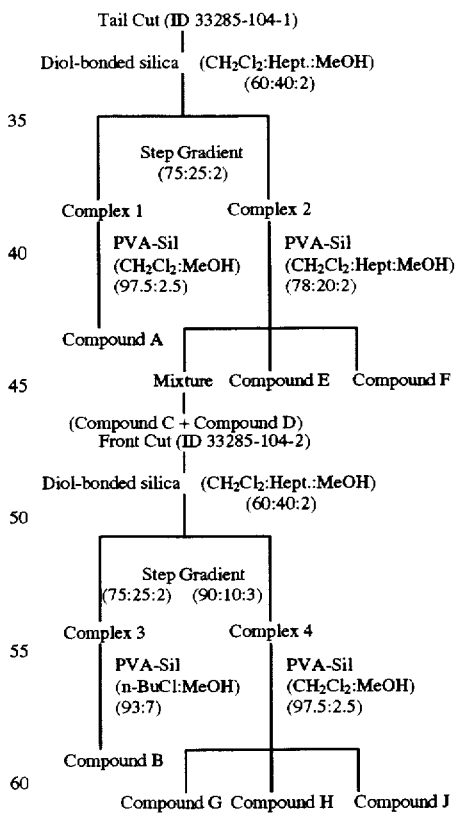

PHYSICO-CHEMICAL PROPERTIES

All compounds were obtained as white powders after removal of solvents. The compounds are soluble in methanol, dimethyl sulfoxide, ethyl acetate, acetone and chloroform; partially soluble in diethyl ether, dichloromethane and 1-chlorobutane; insoluble in hexane, petroleum ether and water. The physico-chemical properties and spectroscopic data of these compounds of the invention are summarized in Table 1.

TABLE 1

| Physico-chemical properties and spectral data of Compounds of the Invention | | | | | |
|---|---|---|---|---|---|
| | Compound A | Compound B | Compound C | Compound D | Compound E |
| $[\alpha]^{20}D$ (c0.1, MeOH) | $-48.4°$ | $-45.2°$ | —ᵃ | —ᵃ | $-47.2°$ |
| UV max.(nm) | 211 | 211 | 211 | 211 | 211 |
| | 268 | 265 | 268 | 268 | 268 |
| | 309 | 305 | 307 | 307 | 305 |
| IR max. (cm$^{-1}$) | 3454, 2939, 1734 | 3430, 2940, 1729 | 3447, 2939, 1730 | 3447, 2939, 1730 | 3431, 2939, 1729 |
| | 1653, 1544, 1457 | 1622, 1544, 1456 | 1652, 1623, 1544 | 1652, 1623, 1544 | 1652, 1623, 1544 |
| | 1384, 1258, 1128 | 1384, 1258, 1103 | 1455, 1384, 1343 | 1455, 1384, 1343 | 1455, 1384, 1257 |
| | 1065, 1030, 990 | 1035 | 1258, 1102, 1037 | 1258, 1102, 1037 | 1125, 1037 |

Figure 2:
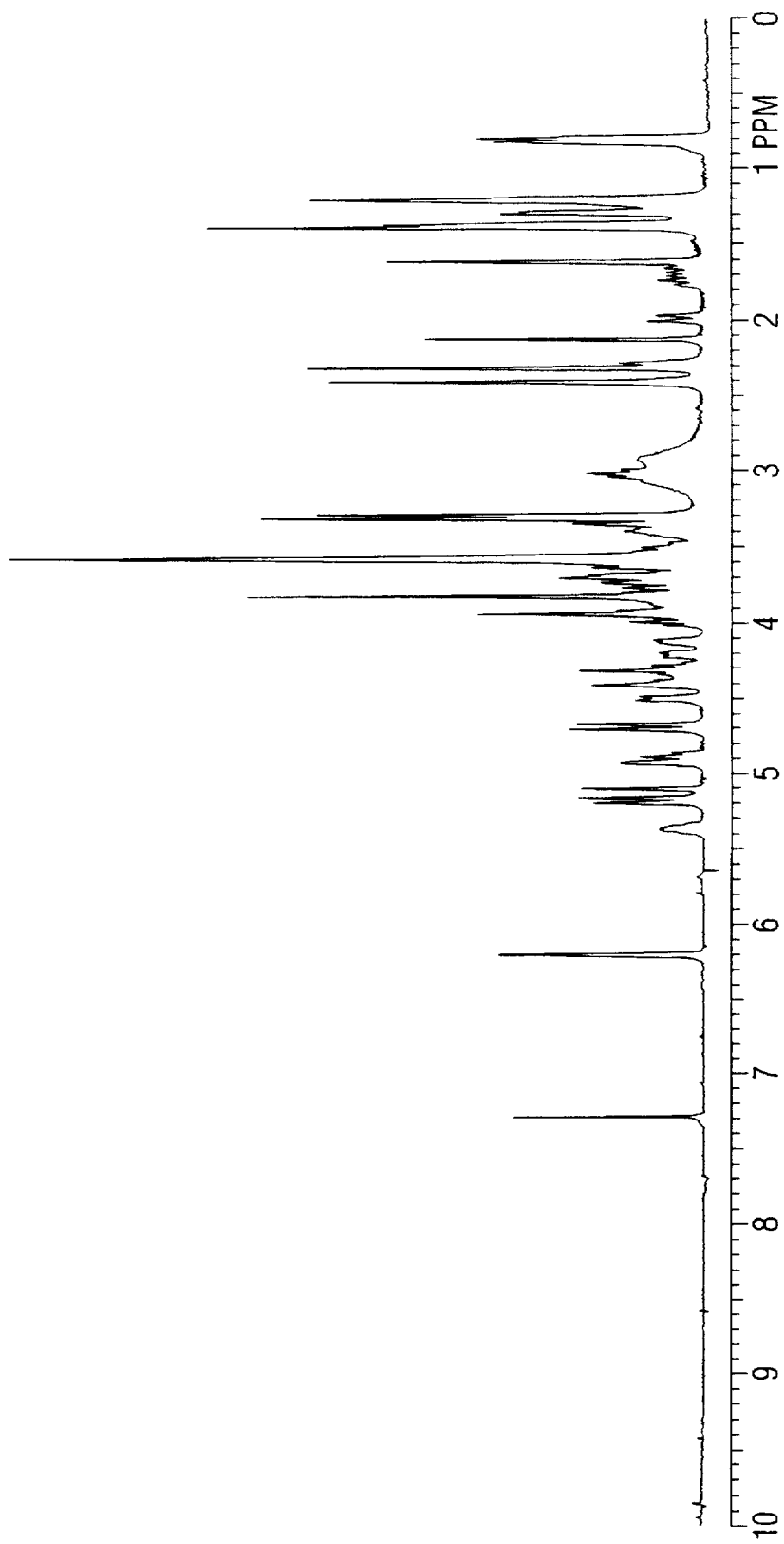
Figure 3:
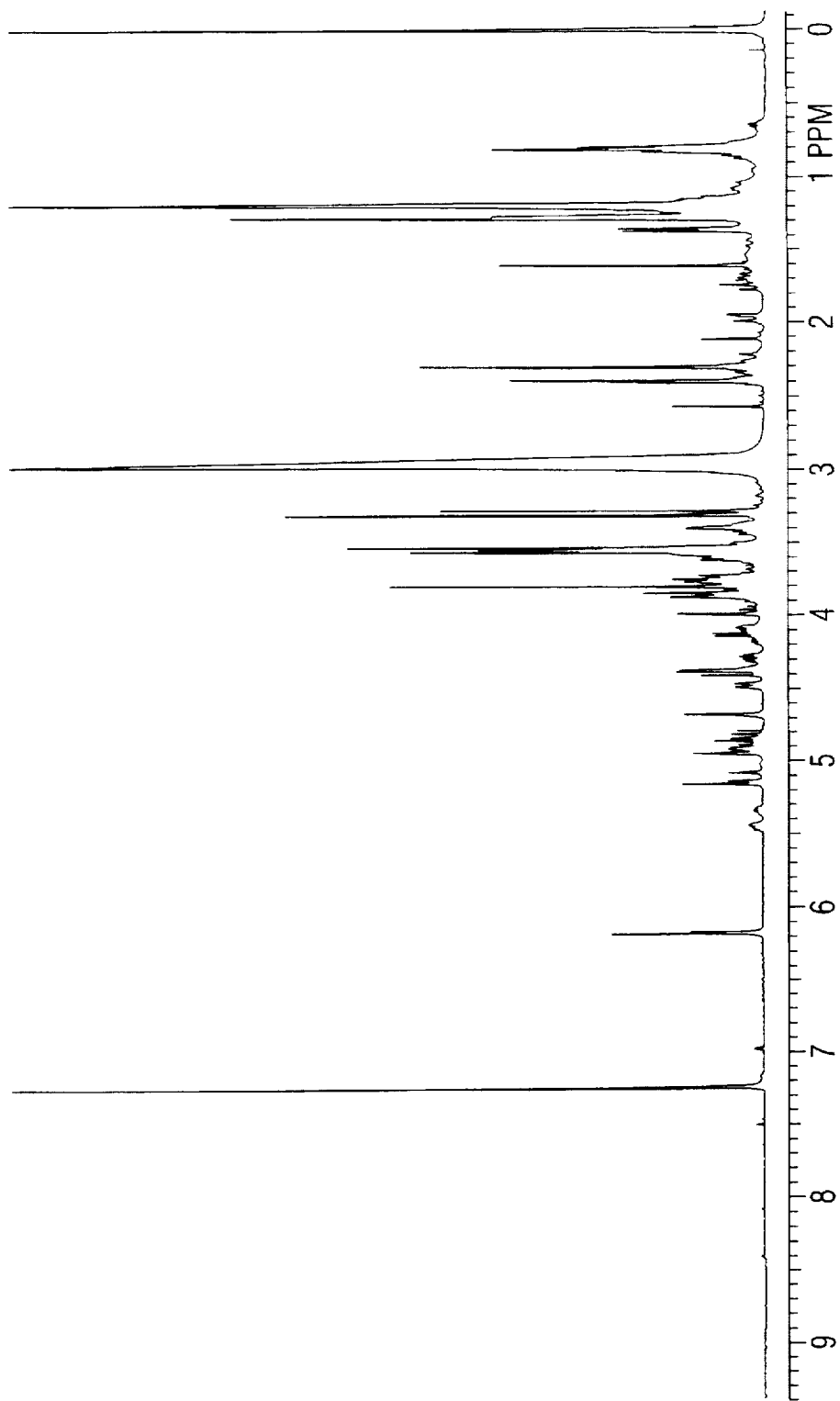
FIG. 3 is a proton NMR spectra for a mixture Compounds C and D.
Figure 4:
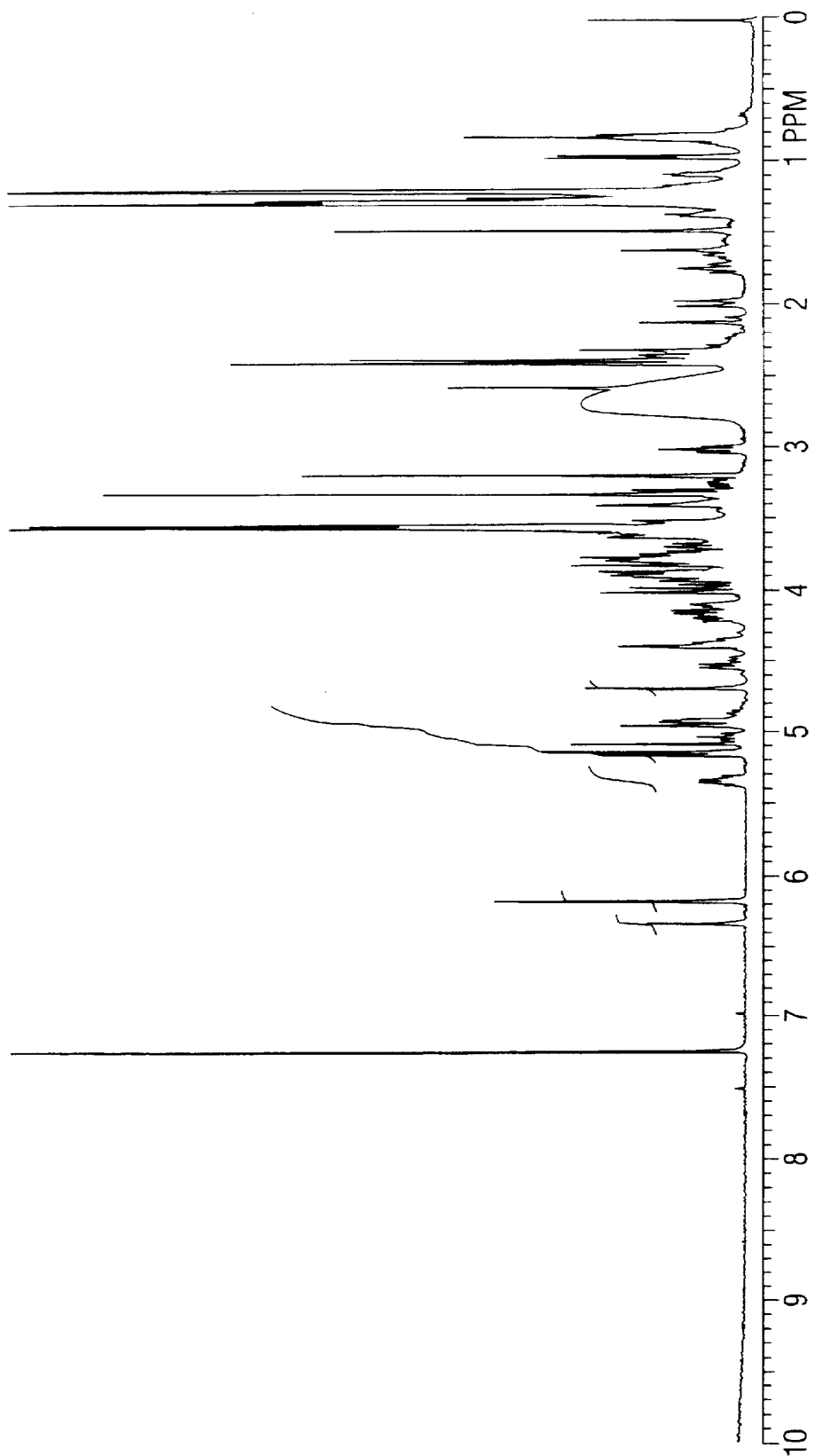

| Physico-chemical properties and spectral data of Compounds of the Invention (ctd.) | | | | | |
|---|---|---|---|---|---|
| | Compound A | Compound B | Compound C | Compound D | Compound E |
| Molecular Weight | 1663 | 1627 | 1645 | 1643 | 1581 |
| FAB Mass Spec. | 1664 (M + H)$^+$ | 1628 (M + H)$^+$ | 1646 (M + H)$^+$ | 1644 (M + H)$^+$ | 1582 (M + H)$^+$ |
| Molecular Formula | $C_{70}H_{96}NO_{38}Cl_3$ | $C_{70}H_{95}NO_{38}Cl_2$ | $C_{71}H_{101}NO_{38}Cl_2$ | $C_{71}H_{99}NO_{38}Cl_2$ | $C_{69}H_{96}NO_{38}Cl$ |
| $^{13}C$ NMR (CDCl$_3$)$^b$ | 120.9 ppm | 120.9 ppm | 120.9 ppm | 120.2 ppm | 120.2 ppm |
| | 118.9 ppm | 118.9 ppm | 119.0 ppm | 118.9 ppm | 119.0 ppm |
| $^1H$ NMR (CDCl$_3$) | FIG. 1 | FIG. 2 | FIG. 3$^c$ | FIG. 3$^c$ | FIG. 4 |

Figure 5:
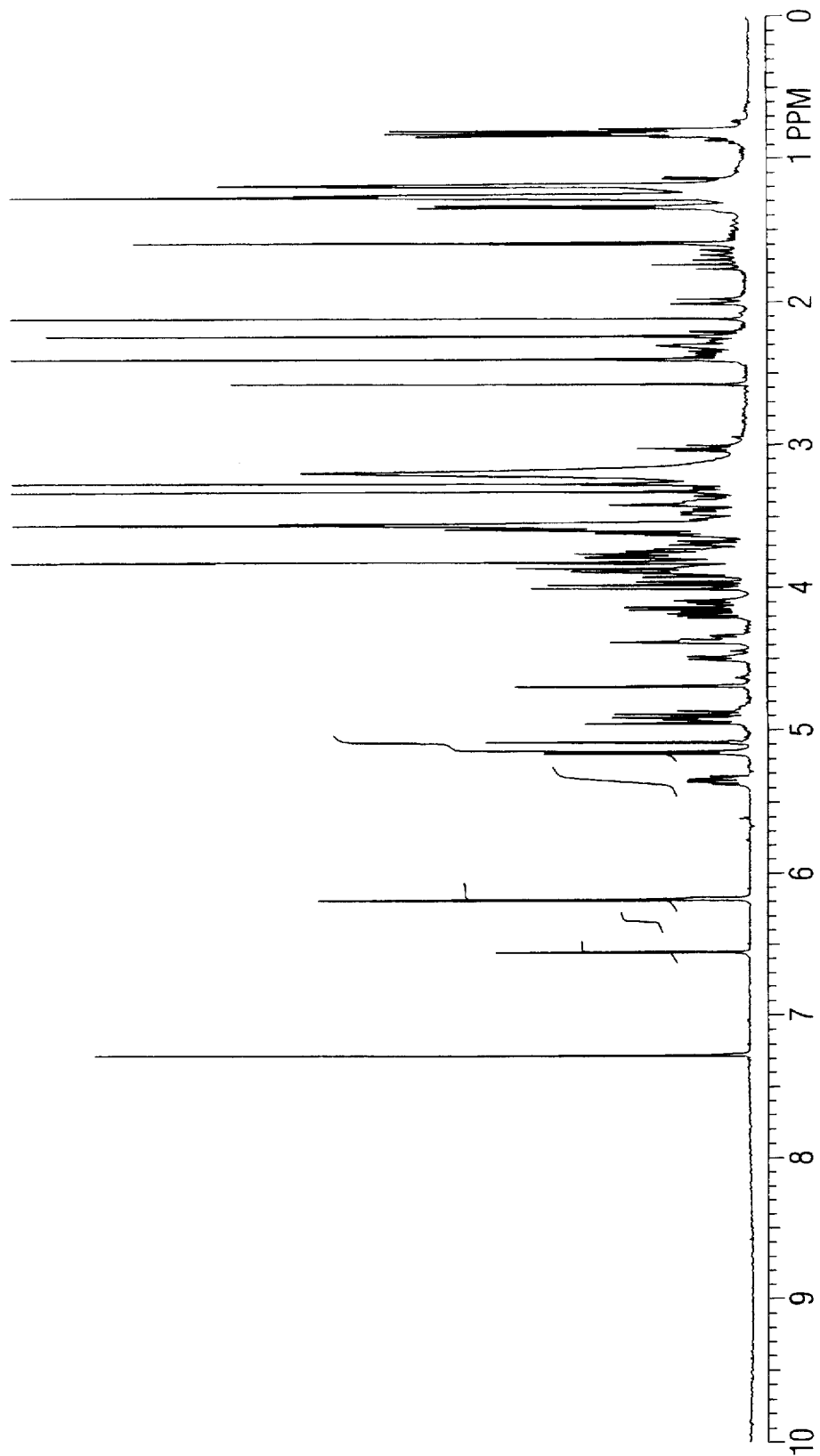
Figure 6:
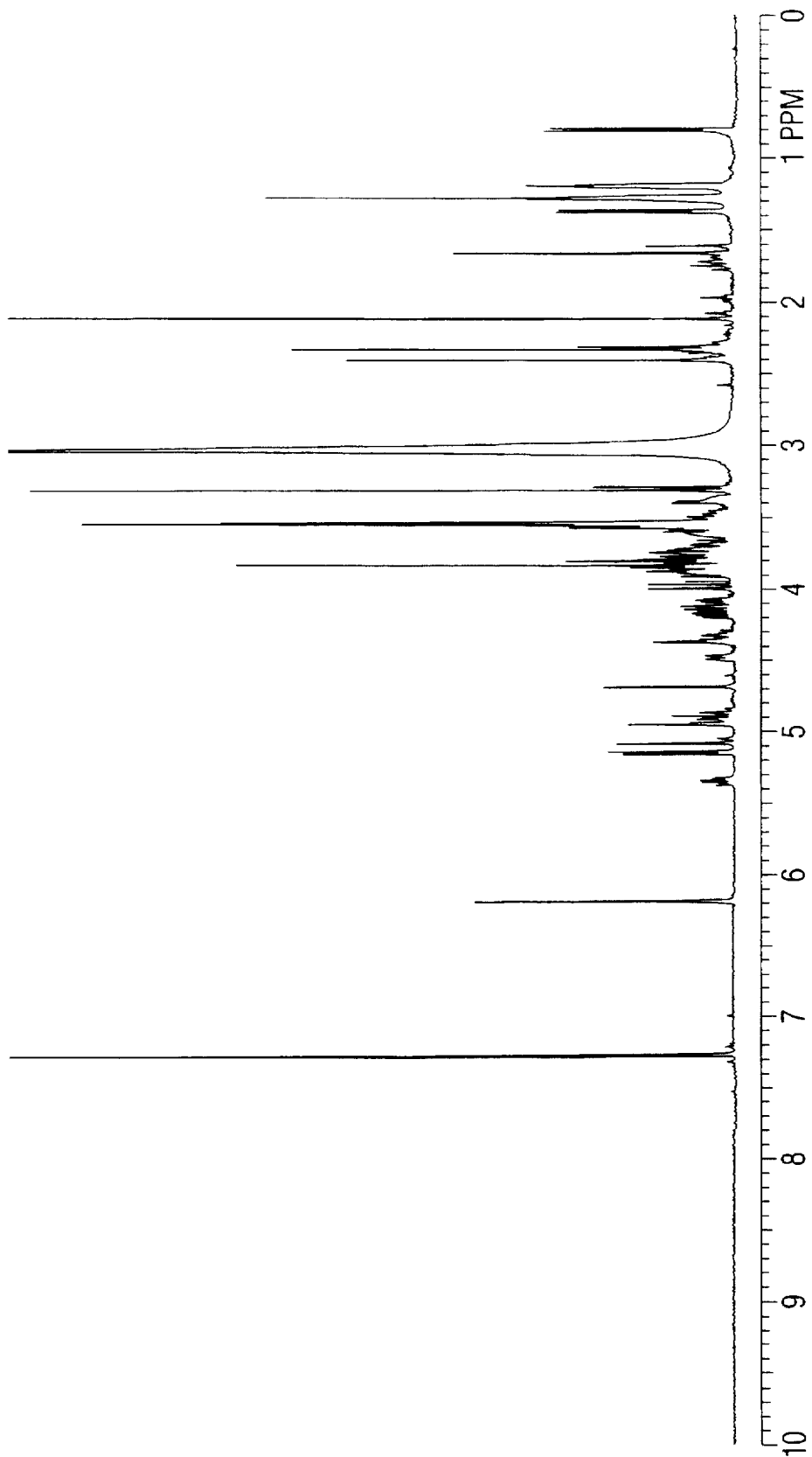
Figure 7:
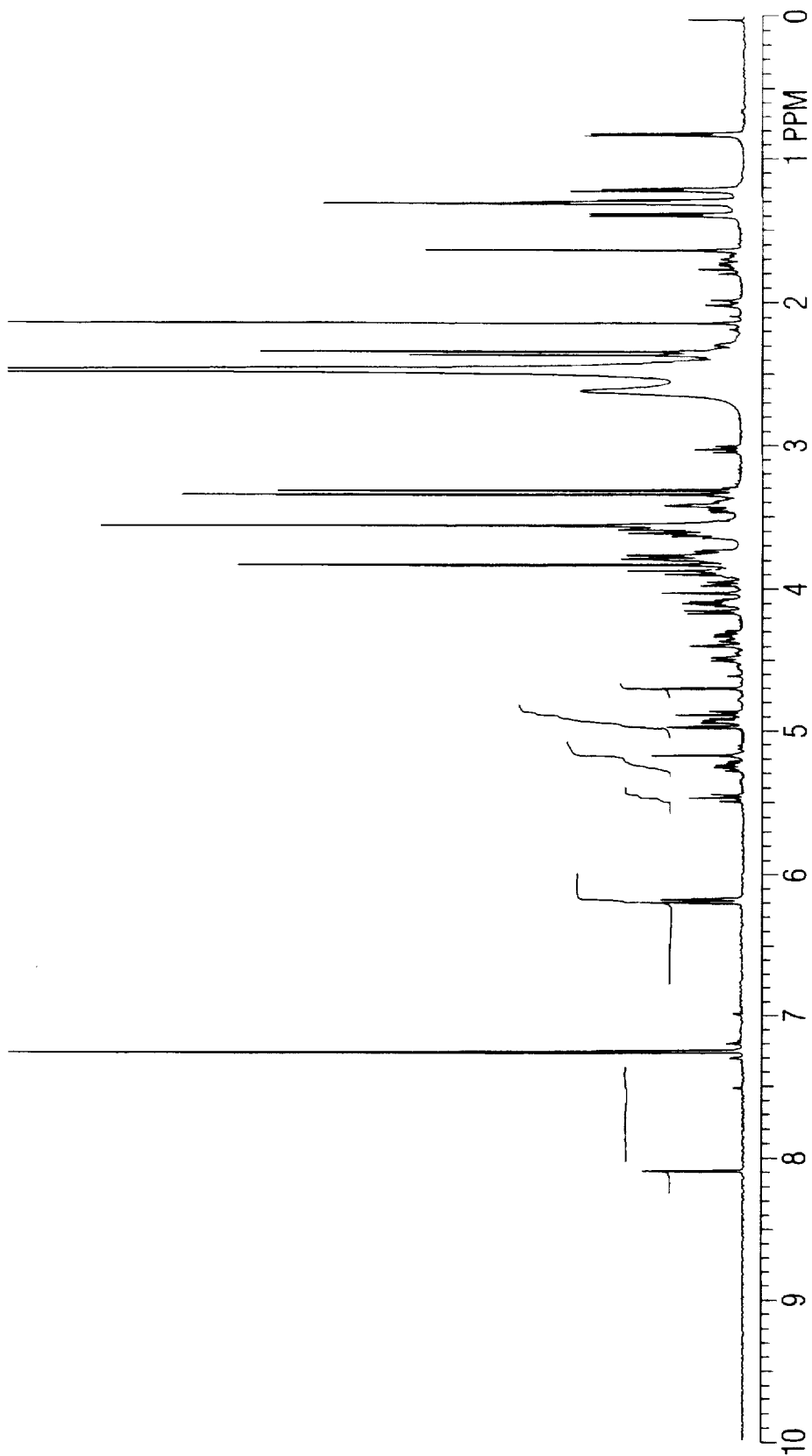
Figure 8:
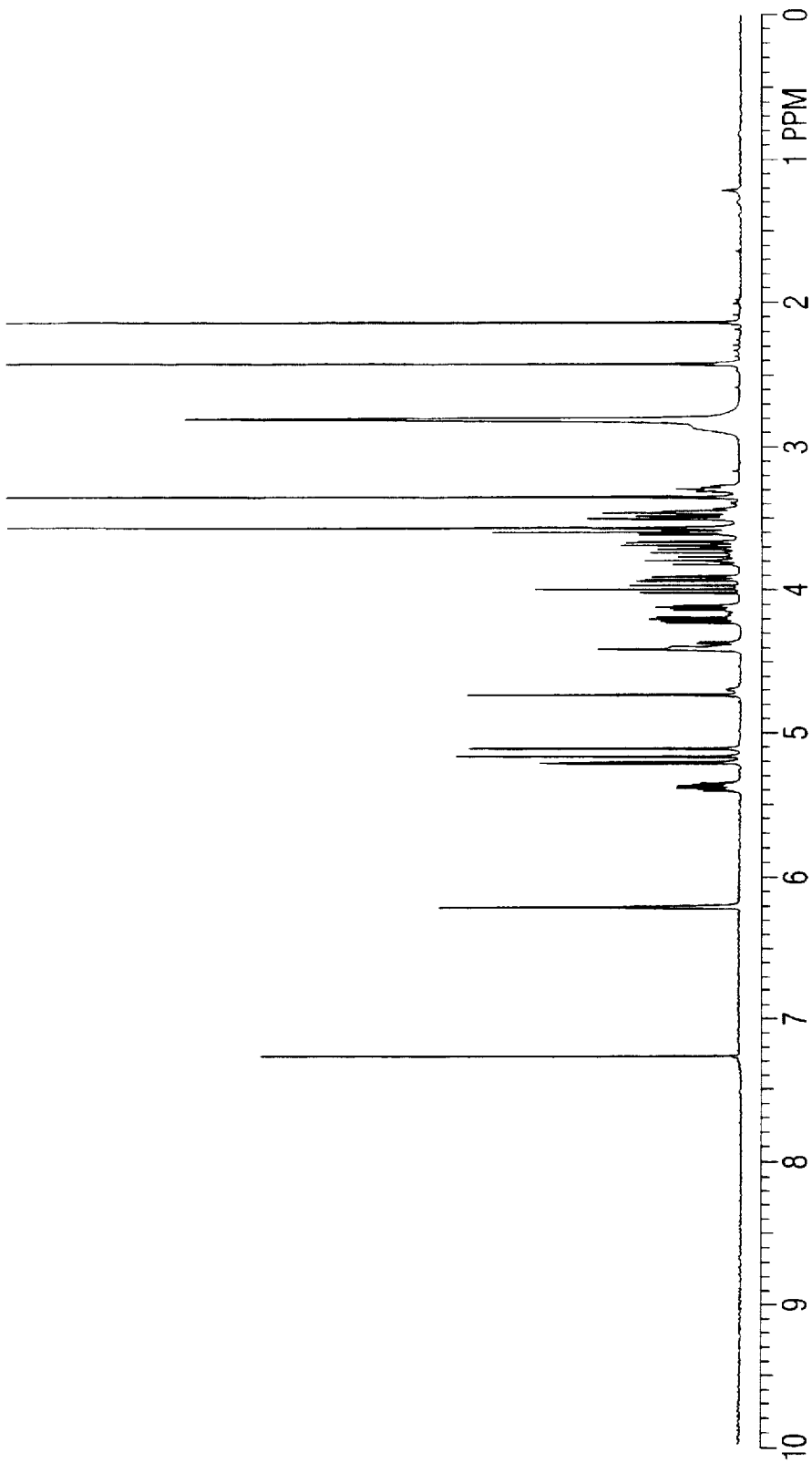

| Physico-chemical properties and spectral data of Compounds of the Invention(Ctd.) | | | | |
|---|---|---|---|---|
| | Compound F | Compound G | Compound H | Compound J |
| $[\alpha]^{20}D$ (MeOH) | $-47.0°$ | $-45.5°$ | $-45.8°$ | $-72.3°$ |
| UV max. (nm) | 211 | 211 | 213 | 210 |
| | 264 | 265 | 265 | 265 |
| | 305 | 305 | 303 | 305 |
| IR max. (cm$^{-1}$) | 3477, 2936, 1728 | 3434, 2939, 1734 | 3430, 2937, 1734 | 3459, 2935, 1653 |
| | 1652, 1622, 1544 | 1652, 1622, 1544 | 1653, 1623, 1543 | 1623, 1452, 1315, |
| | 1457, 1384, 1341 | 1454, 1384, 1257 | 1457, 1385, 1345 | 1262, 1173, 1101 |
| | 1260, 1128, 1036 | 1102, 1038 | 1258, 1172, 1036 | 1068, 1034, 992 |
| Molecular Weight | 1595 | 1615 | 1645 | 632 |
| FAB Mass Spec. | 1596 (M + H)$^+$ | 1616 (M + H)$^+$ | 1646 (M + H)$^+$ | 633 (M + H)$^+$ |
| Molecular Formula | $C_{70}C_{98}NO_{38}Cl$ | $C_{69}H_{95}NO_{38}Cl_2$ | $C_{70}H_{97}NO_{39}Cl_2$ | $C_{27}H_{36}O_{17}$ |
| $^{13}C$ NMR (CDCl$_3$)$^b$ | 120.1 ppm | 120.9 ppm | 121.0 ppm | —$^d$ |
| | 118.9 ppm | 119.0 ppm | 119.1 ppm | 119.0 ppm |
| $^1H$ NMR(CDCl$_3$) | FIG. 5 | FIG. 6 | FIG. 7 | FIG. 8 |

ᵃThe optical rotation was not measured due to the mixture of two components.
$^b$Only two important chemical shifts of distinctive ortho-ester carbons were listed.
$^c$FIG. 3 indicated the presence of a mixture of two compounds.
$^d$Compound J possesses only one ortho-ester functionality.

STRUCTURE DETERMINATION OF THE COMPOUNDS OF THE INVENTION

The structures of the compounds were elucidated based on spectroscopic data analyses, including ultraviolet (UV), infrared (IR), Fast Atom Bombardment mass spectrometry (FAB-MS), proton and carbon-13 nuclear magnetic resonance ($^1H$ and $^{13}C$ NMR) methods. These compounds were characterized as novel everninomicin related antibiotics. $^{13}C$ NMR data of two important ortho-esters are listed in Table 1. $^1H$ NMR spectral data of individual compounds are shown in FIGS. 1–8, respectively. Assignments of some important protons and carbons were accomplished by attached proton test (APT), 2-dimensional nuclear Overhauser effect spectroscopy (NOESY), heteronuclear multiple bond correlation (HMBC) and heteronuclear multiple quantum coherence (HMQC) experiments, as well as by a direct comparison of spectral data with the antibiotic (13-384-component-1, everninomicin) claimed in U.S. Pat. No. 4,597,968 as a reference standard.

EXAMPLE 1

The structure elucidation of Compound A was accomplished by analysis of mass and NMR spectroscopic data. The FAB mass spectral data showed a 34 amu increase of molecular weight by comparison with the reference sample (13-384-component-1, everninomicin). A trichloro-containing molecular ion cluster was observed in the FAB mass spectrum. Both observations revealed the presence of a third chlorine atom in Compound A. The attachment of this extra chlorine atom to the aromatic ester fragment on right side of the molecule was determined based on a secondary fragmentation analysis in comparison with the reference sample (13-384-component-1, everninomicin). (DIAGRAM 1). However, the mass spectral data was unable to locate the exact position of the chlorine atom on the aromatic ring. The position of this chlorine at C-58 was further determined on the basis of NMR spectral data, indicating a strong correlation of the proton-60 and methyl protons-62 in NOESY experiments, and a connectivity between the proton-60 and the methyl carbon-62 in HMBC experiments. Therefore, the structure of Compound A was determined to be that shown in DIAGRAM 2. By utilizing the same methodology, structures of other compounds were also elucidated and are illustrated in DIAGRAM 2. Compound C and H are shown in DIAGRAM 3. It should be noted that Compound J was characterized as a relatively small disaccharide linked to a bicyclic aromatic ester moiety through an orthoester functionality as shown DIAGRAM 4 below.

DIAGRAM 1

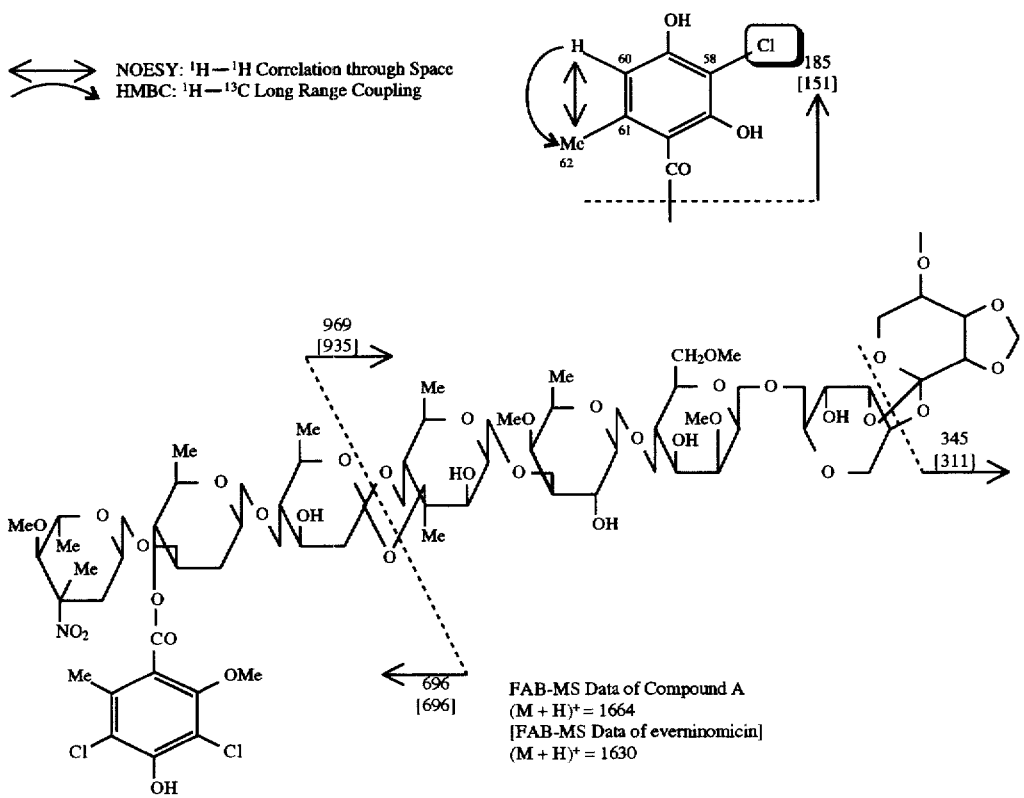

DIAGRAM 2

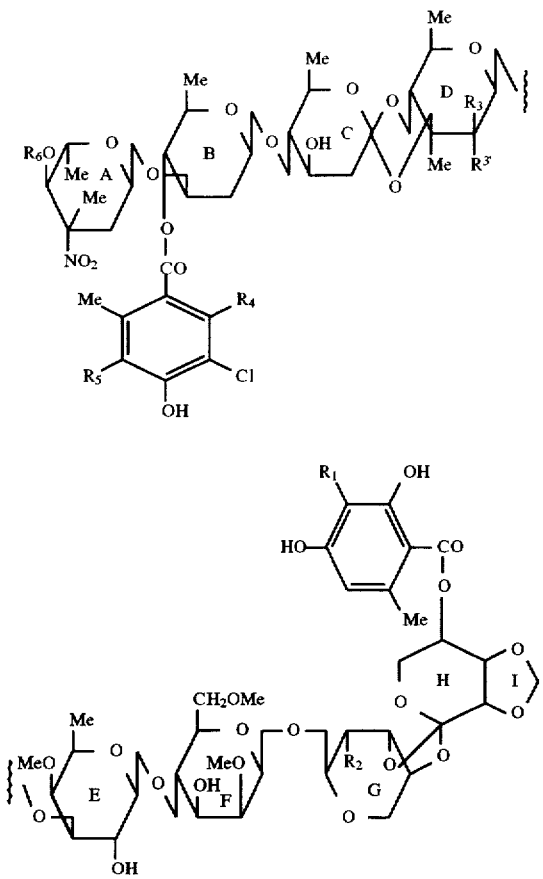

|  | | $R_1$ | $R_2$ | $R_3, R_{3'}$ | $R_4$ | $R_5$ | $R_6$ |
|---|---|---|---|---|---|---|---|
| evernino micin* | | — | H | OH | OH, H | OMe | Cl | Me |
| Compd | A | Cl | OH | OH, H | OMe | Cl | Me |
| Compd | B | H | OH | =O | OMe | Cl | Me |
| Compd | D | H | OMe | OH, H | OMe | Cl | Me |
| Compd | E | H | OH | OH, H | OH | H | Me |
| Compd | F | H | OH | OH, H | OMe | H | Me |
| Compd | G | H | OH | OH, H | OMe | Cl | H |

*Everninomicin is the antibiotic 13-384, component 1, as disclosed in U.S. Pat. No. 4,597,968

The italicized, capital letters identify the rings in the compounds of the invention The structures for compounds C and H are shown just below.

Diagram 3

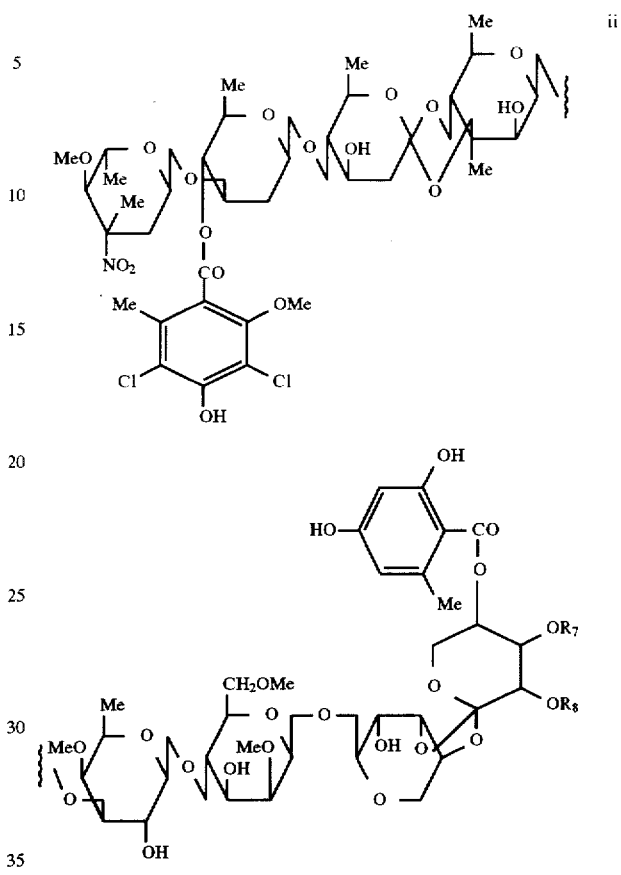

Compound C   $R_7 = CH_3$;   $R_8 = CH_3$.
Compound H   $R_7 = C(O)H$;   $R_8 = H$.

The structure for compound J is shown just below in Diagram 4.

DIAGRAM 4

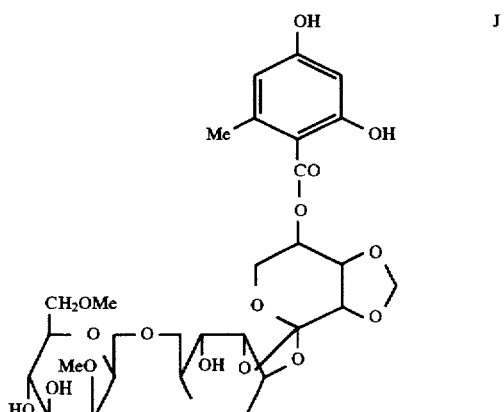

BIOLOGICAL PROPERTIES OF THE COMPOUNDS OF THE INVENTION

The minor components were tested for activity based on an agar disk-diffusion protocol. Each component was dissolved at 1 mg/mL in $CH_2Cl_2$:MeOH (95:5 v/v) and a ten fold dilution made in the same vehicle. Twenty microliters of each concentration was transferred to an 8 mm standard paper disk and allowed to air dry for thirty minutes. Each set of disks were placed on agar seeded with *Staphylococcus aureus* at two pH's (7s) and incubated overnight at 35° C. Zones of sizes of inhibition are given below as the diameter of the circle of inhibition and are given in millimeters. The results are tabulated below:

| | Amount | | | |
|---|---|---|---|---|
| | 20 µg | 2 µg | 20 µg | 2 µg |
| Everninomicin | 21 | 19 | 26 | 23 |
| Compound A | 20 | 20 | 26 | 23 |
| Compound B | 14 | 12 | 17 | 13 |
| Compound C/D | 20 | 16 | 22 | 17 |
| Compound E | 18 | 16 | 22 | 17 |
| Compound F | 17 | 16 | 20 | 17 |
| Compound G | NT | NT | NT | NT |
| Compound H | NT | NT | NT | NT |
| Compound J | 0 | 0 | 10 | 0 |

As used herein, NT means not tested.

The nearly equivalent potency of Compound A with everninomicin was further documented on a four fold dilution.

In vivo antibiotic activity of the compounds of the invention can be demonstrated in mice via subcutaneous administration.

This invention may be carried out using pharmaceutically acceptable compositions comprising a pharmaceutically acceptable carrier and one or more compounds selected from the group consisting of A, B, C, D, E, F, G, H and J.

As such, the antibiotics may be administered with any suitable pharmaceutical carrier and administered orally, parenterally or topically in a variety of formulations. For oral administration, the antibiotics of this invention may be compounded in the form of tablets capsules, elixirs and the like. Tablets and capsules may contain such excipients as starch or lactose; liquid forms may contain coloring or flavoring agents. Topical preparations may be in the form of creams, hydrophobic or hydrophilic ointments or aqueous, non-aqueous emulsion-type lotions. Typical carriers for such formulations are water, oils, greases, polyesters, and polyols. Parenteral formulations, e.g. injectible dosage forms are usually liquids such as solutions or suspensions with typical carriers being distilled water or saline solution.

The dose to be administered in any particular dosage form will depend on various factors, such as the characteristics of the animal species being treated, the susceptibility of the infecting organism to the antibiotic, and the stage and severity of the infection. Generally, the dosage administered is from about 1.0 mg to about 25 mg/kg of body weight per day, in divided dosages, the specified dosage being left to the discretion of the practitioner.

In treating certain patients with the compounds of this invention, it is possible to include other pharmaceutically active ingredients in the dosage unit.

THE MICROORGANISM

The microorganism used to obtain the compounds of this invention is a mutant strain of *Micromonospora Carbonacea var Africana* as set forth in U.S. Pat. No. 4,597,968 which is hereby incorporated by reference. The way in which this mutant strain is obtained is as set forth in this application.

The mutant strain of *Micromonospora Carbonacea var Africana* was prepared as set forth just below. Initially, parent strain SCC 1413 was subject to N-nitrosoguanidine (NTG) mutagenesis resulting in greater than a 90% kill of the culture. Fifteen hundred surviving isolates were examined for enhanced biological activity against *S. aureus* and *E. coli*. Single colony isolates were germinated in test tubes containing 10 mL of germination media and shaken at 250 r.p.m. on a gyratory shaker at 30° C. for 48 hours. Fermentation studies were initiated by transferring 2.5 mL of the seed to 250 mL Erlenmeyer flasks containing 50 mL of fermentation media and incubating at 30° C. for 96 hours at 250 r.p.m. on a gyratory shaker. SCC 1631 was identified as an improved producer of the 13-384 complex on the basis of its improved bioactivity against *S. aureus* and *E. coli*.

Strain SCC 1756 was isolated by NTG mutation of SCC1631 followed by selection of the isolates on agar plates containing 150 µg/mL of everninomicin(complex of nitro and nitroso analogs). Strain SCC 2146 was obtained by NTG mutagenesis of SCC 1756. Except for isolating the NTG mutagenized strains of SCC 1631 on the high levels of everninomicin (complex of nitro and nitroso analogs), the protocols for both mutation studies were as previously described. For the latter two mutation studies, fermentation broths were extracted with ethyl acetate and the concentrates were chromatographed on Whatman LKGDF thin layer plates in a solvent system consisting of chloroform:methanol (9:1) followed by bioautography against *S. aureus* and *E. coli* to confirm the production of all components of the antibiotic complex. To follow the increased titres of everninomicin (complex of nitro and nitroso analogs), thin layer plates were examined by using the Shimadzu CS-930 TLC plate scanner and quantitating the higher producing extracts using HPLC. Combined titers are defined as the sum of everninomicin nitro and nitroso analogs.

What is claimed is:
1. A compound of the formula

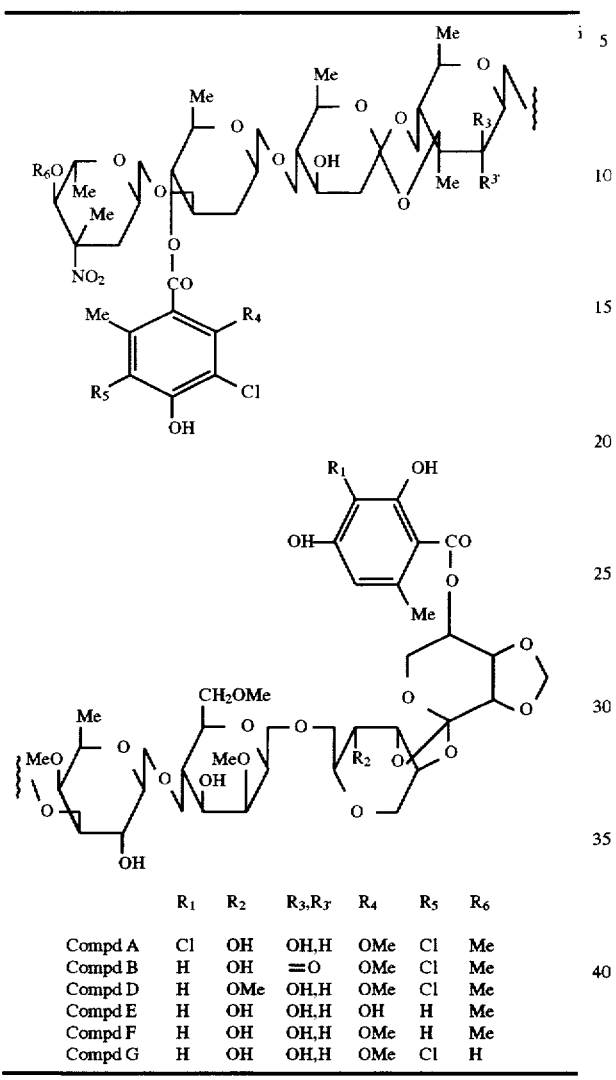

| | $R_1$ | $R_2$ | $R_3,R_3'$ | $R_4$ | $R_5$ | $R_6$ |
|---|---|---|---|---|---|---|
| Compd A | Cl | OH | OH,H | OMe | Cl | Me |
| Compd B | H | OH | =O | OMe | Cl | Me |
| Compd D | H | OMe | OH,H | OMe | Cl | Me |
| Compd E | H | OH | OH,H | OH | H | Me |
| Compd F | H | OH | OH,H | OMe | H | Me |
| Compd G | H | OH | OH,H | OMe | Cl | H | or a pharmaceutically acceptable salt thereof.

2. Compound A according to claim 1 wherein $R_1$ is Cl, $R_2$ is OH, $R_3$ is OH, $R_3'$ is H, $R_4$ is OMe, $R_5$ is Cl and $R_6$ is Me; or a pharmaceutically acceptable salt thereof.

3. Compound B according to claim 1 wherein $R_1$ is H, $R_2$ is OH, $R_3$ and $R_3'$ taken together are =O, $R_4$ is OMe, $R_5$ is Cl and $R_6$ is Me; or a pharmaceutically acceptable salt thereof.

4. Compound D according to claim 1 wherein $R_1$ is H, $R_2$ is OMe, $R_3$ is OH, $R_3'$ is H, $R_4$ is OMe, $R_5$ is Cl and $R_6$ is Me; or a pharmaceutically acceptable salt thereof.

5. Compound E according to claim 1 wherein $R_1$ is H, $R_2$ is OH, $R_3$ is OH, $R_3'$ is H, $R_4$ is OH, $R_5$ is H and $R_6$ is Me; or a pharmaceutically acceptable salt thereof.

6. Compound F according to claim 1 wherein $R_1$ is H, $R_2$ is OH, $R_3$ is OH, $R_3'$ is H, $R_4$ is OMe, $R_5$ is H and $R_6$ is Me; or a pharmaceutically acceptable salt thereof.

7. The Compound G according to claim 1 wherein $R_1$ is H, $R_2$ is OH, $R_3$ is OH, $R_3'$ is H, $R_4$ is OMe, $R_5$ is Cl and $R_6$ is H; or a pharmaceutically acceptable salt thereof.

8. A compound of the formula

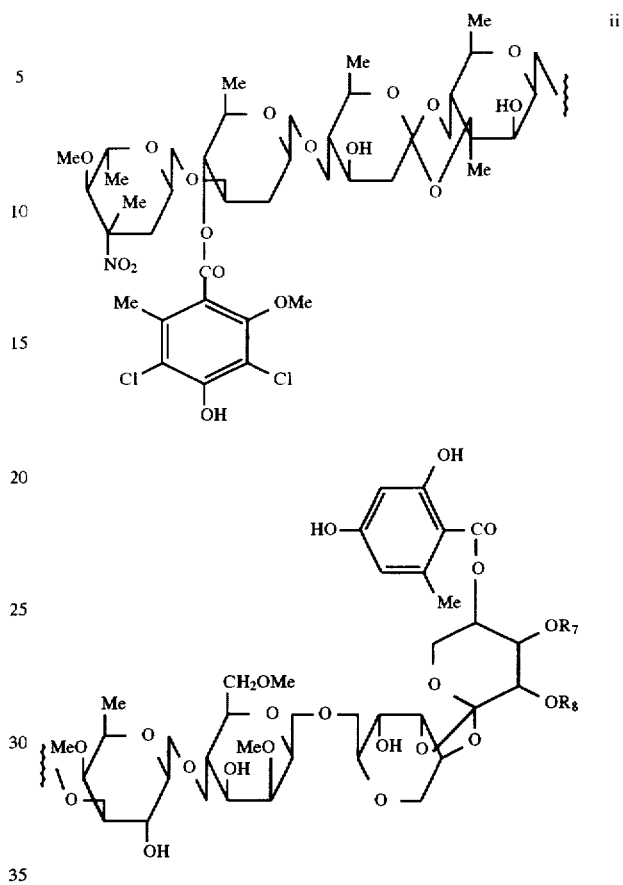

wherein $R_7 = CH_3$; $R_8 = CH_3$; (Compound C) or
$R_7 = C(O)H$; $R_8 = H$ (Compound H).

or a pharmaceutically acceptable salt thereof.

9. The Compound C according to claim 8 wherein $R_7$ is $CH_3$, and $R_8$ is $CH_3$; or a pharmaceutically acceptable salt thereof.

10. A The Compound H according to claim 8 wherein $R_7$ is C(O)H and $R_8$ is H; or a pharmaceutically acceptable salt thereof.

11. The compound of the formula

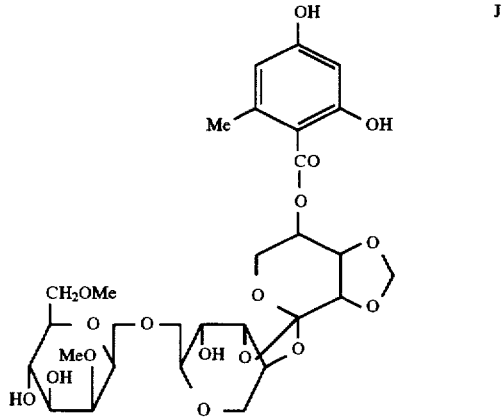

or a pharmaceutically acceptable salt thereof.

12. A composition comprising a compound according to claim 1 and a pharmaceutically acceptable carrier material.

13. A composition comprising a compound according to claim 8 and a pharmaceutically acceptable carrier material.

14. A method for treating bacterial infections in a mammal which comprises administering to the mammal in need thereof, an antibacterially effective amount of a compound according to claim 1.

15. A method for treating bacterial infections in a mammal which comprises administering to the mammal in need thereof an antibacterially effective amount of a compound according to claim 8.

* * * * *